(12) United States Patent
Yuan et al.

(10) Patent No.: US 12,144,543 B2
(45) Date of Patent: Nov. 19, 2024

(54) MULTIFUNCTIONAL LASER SCALPEL AND LASER PROCESSING DEVICE COMPRISING CONTROLLABLY SELF-DEFORMABLE OPTICAL FIBER

(71) Applicant: Peking University School of Stomatology, Beijing (CN)

(72) Inventors: Fusong Yuan, Beijing (CN); Peijun Lyu, Beijing (CN); Shanshan Liang, Beijing (CN)

(73) Assignee: Peking University School of Stomatology, Beijing (CN)

( * ) Notice: Subject to any disclaimer, the term of this patent is extended or adjusted under 35 U.S.C. 154(b) by 645 days.

(21) Appl. No.: 17/194,306

(22) Filed: Mar. 7, 2021

(65) Prior Publication Data

US 2021/0186611 A1 Jun. 24, 2021

Related U.S. Application Data

(63) Continuation of application No. PCT/CN2019/086575, filed on May 13, 2019.

(30) Foreign Application Priority Data

Mar. 25, 2019 (CN) .......................... 201910228245.2

(51) Int. Cl.
*A61B 18/22* (2006.01)
*B23K 26/70* (2014.01)
*G02B 6/036* (2006.01)
*G02B 6/44* (2006.01)

(52) U.S. Cl.
CPC .............. *A61B 18/22* (2013.01); *B23K 26/70* (2015.10); *G02B 6/036* (2013.01); *G02B 6/443* (2013.01); *A61B 2018/2205* (2013.01)

(58) Field of Classification Search
CPC A61B 18/22; A61B 2018/2205; G02B 6/443; G02B 6/036; B23K 26/70
See application file for complete search history.

(56) References Cited

U.S. PATENT DOCUMENTS

| 2010/0228238 | A1* | 9/2010 | Brennan | A61B 5/0073 600/476 |
| 2013/0237976 | A1* | 9/2013 | Temelkuran | A61B 18/24 606/16 |
| 2019/0258091 | A1* | 8/2019 | Kliner | B23K 26/0342 |

FOREIGN PATENT DOCUMENTS

| CN | 1049781 A | | 3/1991 |
| CN | 101852886 A | | 10/2010 |
| CN | 103293593 A | * | 9/2013 |
| CN | 104013377 A | | 9/2014 |
| CN | 109452969 B | | 9/2019 |

* cited by examiner

*Primary Examiner* — Lynsey C Eiseman
*Assistant Examiner* — Amanda L Steinberg

(57) ABSTRACT

Provided are a controllably self-deformable optical fiber, a multifunctional laser scalpel and a laser processing device including the same. The controllably self-deformable optical fiber drives the protective layer and the optical fiber to deform through controllable deformation of a deformation portion on an outer surface of the protective layer. In addition, the optical fiber also has multiple functions, and can be applied in the treatment of complex lacunae in medical and other related fields.

12 Claims, 2 Drawing Sheets

MULTIFUNCTIONAL LASER SCALPEL AND LASER PROCESSING DEVICE COMPRISING CONTROLLABLY SELF-DEFORMABLE OPTICAL FIBER

CROSS-REFERENCE TO RELATED APPLICATIONS

This application is a continuation of International Application No. PCT/CN2019/086575, filed on May 13, 2019, which claims the benefit of priority from Chinese Patent Application No. 201910228245.2, filed on Mar. 25, 2019. The content of the aforementioned applications, including any intervening amendments thereto, is incorporated herein by reference.

TECHNICAL FIELD

This application relates to an optical fiber, and more particularly to a controllably self-deformable optical fiber, and a multifunctional laser scalpel and a laser processing device comprising the same.

BACKGROUND

As one of the greatest scientific inventions in the 20th century, laser technology greatly promotes the convenience of human life and has been widely used in scientific researches, production and daily life. For example, lasers are widely applied in the medical treatment.

In the early 1990s, photorefractive keratectomy (PRK) was performed in clinic by U.S. Food and Drug Administration (FDA) to treat myopia. At present, the laser is commonly applied in ophthalmology for myopia surgery and corneal transplantation surgery (or keratoplasty). In addition, the laser can be used for resection of soft tissue lesions and cosmetic operations in surgery. For the current oral treatment, there are three main types of lasers, including: (1) lasers for treating soft tissues and some hard tissues in the oral lacuna, such as Neodymium-doped Yttrium Aluminium Garnet (Nd:YAG) lasers, $CO_2$ lasers and gallium-aluminium-arsenic (GaAlAs) lasers; (2) lasers for treating dental hard tissues, such as erbium-doped Yttrium Aluminium Garnet (Er:YAG) lasers and Transversely-Excited Atmospheric-Pressure (TEA) $CO_2$ lasers; and (3) lasers for treating soft and hard tissues in the oral lacuna, especially for the rapid cutting of dental hard tissues, such as Erbium, Chromium: Yttrium-Scandium-Gallium-Garnet (Er, Cr:YSGG) laser systems. However, most of these lasers emit continuous laser, which will easily cause a temperature rise, thereby damaging normal tissues.

In recent years, the improvement of mode-locking in solid-state lasers makes it easier to obtain an ultrashort pulse laser. The ultrashort pulse laser has high beam quality and high-peak power and thus is considered to be an ideal ultra-precision surgical scalpel. In addition, due to the absence of heat-affected zone, fast cutting speed, smooth cutting edge and desirable effect, the ultrashort pulse laser has been rapidly applied in many fields, such as dental surgery. It has been demonstrated that the ultrashort pulse laser not only can enhance the structural strength of the teeth surface, but also will not cause micro cracks and other damages on the teeth. Unfortunately, the current ultrashort pulse laser with high peaks can only be transmitted through a bulky light guide arm, thereby greatly limiting its application in various fields. Conceivably, in the endodontic treatment, the bulky light guide arm will render the ultrashort pulse laser hard to reach the narrow and curved cavities to precisely cut tissues.

SUMMARY

This disclosure provides a controllably self-deformable optical fiber and a multifunctional laser scalpel and a laser processing device comprising the same to overcome the defect in the prior art that the existing light guide arm is too large in size to allow the ultrashort pulse laser to reach narrow and curved cavities.

In a first aspect, this application provides a controllably self-deformable optical fiber, comprising:
a core layer;
a protective layer; and
a controllably self-deformable element;
wherein the core layer comprises a fiber core and is provided inside the protective layer; and the controllably self-deformable element is attached to an outer surface of the protective layer.

In an embodiment, the fiber core is a high-power laser fiber core, preferably a hollow fiber.

In an embodiment, the controllably self-deformable optical fiber also comprises an intermediate layer; the intermediate layer is provided between the core layer and the protective layer; and a plurality of conduits which are parallel to a length direction of the core layer are provided in the intermediate layer.

In an embodiment, the plurality of conduits comprise a lighting fiber conduit; and a lighting fiber core is provided in the lighting fiber conduit.

In an embodiment, the plurality of conduits comprise an imaging fiber conduit; and an imaging fiber core is provided in the imaging fiber conduit.

In an embodiment, the plurality of conduits comprise at least one feed-discharge conduit for liquid and gas.

In an embodiment, the plurality of conduits comprise an electrical conduit; a sensor is provided at a tail end of the electrical conduit; and an electrical wire of the sensor is laid in the electrical conduit.

In an embodiment, the fiber core is in slidable fit with the protective layer or the intermediate layer.

In an embodiment, there are at least one controllably self-deformable elements; the at least one controllably self-deformable element is evenly or unevenly attached to the outer surface of the protective layer; and the at least one controllably self-deformable element is individually or jointly controlled to generate deformation.

In an embodiment, the controllably self-deformable element is made of a metal, a polymer or a biological material that is capable of stretching, bending, tightening, expanding and/or rotating, under the exposure to sound, light, electricity, heat, magnetism and/or chemical substances.

In a second aspect, this application further provides a laser scalpel, comprising the controllably self-deformable optical fiber of the first aspect.

In a third aspect, this application further provide a laser processing device, comprising the controllably self-deformable optical fiber of the first aspect.

Compared to the prior art, this application has the following beneficial effects.

In the disclosure, a protective layer is provided outside the fiber core, and a controllably self-deformable element is attached to an outer surface of the protective layer. The controllable deformation of the controllably self-deformable element can drive the controllably self-deformable optical fiber to bend or rotate, so as to replace the light guide arm of the prior art. Compared to the existing light guide arm, the controllably self-deformable optical fiber has a more exquisite structure and a smaller size. Therefore, the controllably self-deformable optical fiber, especially the fiber core, can reach narrow and curved cavities to cut tissues precisely.

In addition, the multifunctional composite optical fiber provided herein, including a lighting fiber core, an imaging fiber core and a feed-discharge conduit for liquid and gas, is capable of precisely controlling the deformation, and also has the functions of real-time visual monitoring, ablation, cleaning and disinfection, and quantitative delivery or discharge of gases or liquids.

BRIEF DESCRIPTION OF THE DRAWINGS

The drawings described here are intended to facilitate further understanding of the present disclosure. Obviously, the described embodiments are merely illustrative of the present disclosure and are not intended to limit the scope of the present disclosure.

DETAILED DESCRIPTION OF EMBODIMENTS

The present disclosure will be further described in detail with reference to the embodiments and the accompanying drawings, from which objectives, technical solutions and advantages of the present disclosure will be better understood. It should be understood that the embodiments are illustrative of the present disclosure, and are not intended to limit the scope of the present disclosure. The present disclosure can be implemented by those of ordinary skill in the art even without some of these specific details. The following embodiments are merely intended to facilitate the understanding of the present disclosure.

As used herein, terms "include", "comprise" or variations thereof should be interpreted as a non-exclusive inclusion. Specifically, the process, method, article, or apparatus is not limited to the elements listed therein, and should not exclude other elements that are not explicitly listed or inherent elements of the process, method, article or apparatus. Unless specified, the elements defined by the sentence "include . . ." do not exclude the existence of other same elements in the process, method, article, or equipment.

Figure 1:
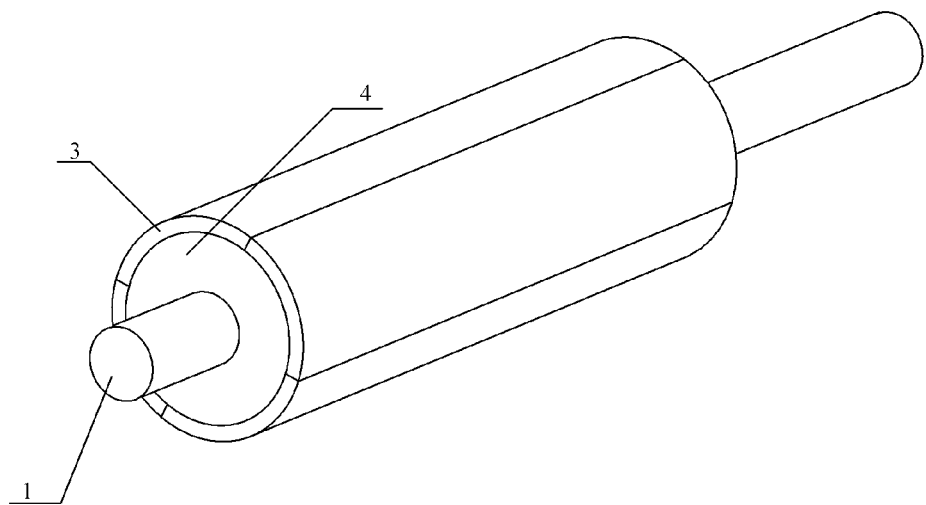
FIG. 1 is a schematic diagram of a controllably self-deformable optical fiber according to an embodiment of the present disclosure.

This embodiment provides a controllably self-deformable optical fiber. FIG. 1 is a schematic diagram of the controllably self-deformable optical fiber according to an embodiment of the present disclosure. As shown in FIG. 1, the controllably self-deformable optical fiber includes a core layer 1, a protective layer 4, and a controllably self-deformable element 3.

The core layer 1 includes a fiber core. An outer surface of the fiber core is also coated with a cladding layer. The core layer 1 is provided inside the protective layer 4 which has a certain strength and resilience and is preferably made of polyethylene. The controllably self-deformable element 3 is attached to an outer surface of the protective layer 4.

A laser emits ultrashort pulse lasers (i.e., femtosecond lasers), and then the ultrashort pulse lasers are conducted to a tail end of the fiber core through the fiber core of the core layer 1. In order to reduce the transmission loss of the ultrashort pulse lasers in the fiber core, the fiber core used in the controllably self-deformable fiber adopts a high-power laser fiber core. In some embodiments, a hollow fiber is adopted. A diameter of the fiber core is 100-300 μm. Compared to a traditional solid fiber, the hollow fiber guides light through air instead of glasses. Therefore, for energy transferring, the hollow fiber is far superior to the traditional solid fiber. In addition, the cladding layer on the outer surface of the hollow fiber can be omitted.

This embodiment also provides a multifunctional composite controllably self-deformable optical fiber. The multifunctional composite controllably self-deformable optical fiber is similar to the controllably self-deformable optical fiber shown in FIG. 1 except that the multifunctional composite controllably self-deformable optical fiber shown in FIG. 2 further includes an intermediate layer 2. The intermediate layer 2 is provided between the core layer 1 and the protective layer 4. A plurality of conduits which are parallel to each other and distributed along a length direction of the core layer 1 are provided inside the intermediate layer 2.

The conduits include, but are limited to, a lighting fiber conduit 21, an imaging fiber conduit 22, a feed-discharge conduit 23 for liquid and gas and an electrical conduit 24.

A lighting fiber core may be arranged in the lighting fiber conduit 21. The lighting fiber core conducts light generated by a light source to a tail end of the lighting fiber conduit 21, so as to realize the illumination of a working surface of the multifunctional composite controllable self-deformable optical fiber.

An imaging fiber core may be arranged in the imaging fiber conduit 22. The imaging fiber core conducts a reflected light from the working surface of the multifunctional composite controllably self-deformable optical fiber to an optical imaging device, so as to realize real-time visual monitoring of the working surface.

The feed-discharge conduit 23 is configured to feed and discharge gases or liquids. There may be one or more feed-discharge conduits 23. For example, a liquid and gas feed conduit and a liquid and gas discharge conduit are provided separately; a liquid feed-discharge conduit and a gas feed-discharge conduit are provided separately; or a liquid feed conduit, a liquid discharge conduit, a gas feed conduit and a gas discharge conduit are provided separately to feed and discharge the gas or the liquid. Depending on specific application scenarios, the gas fed or discharged includes, but is not limited to, cold air, hot air and protective gases; and the liquid fed or discharged includes, but is not limited to, liquid medicine, coolant and glue. It is concluded that the feed-discharge conduit 23 can quantitatively feed and discharge the gas or liquid, thereby realizing functions of, such as cleaning, disinfection, positive and negative pressure control for the working surface and parameter adjustment of working environment of the working surface.

Electrical wires for power supply or data transmission are laid in the electrical conduit 24, so as to allow a sensor to be mounted on a tail end of the electrical conduit 24 near the working surface. The sensor includes, but is not limited to, an image sensor, a temperature sensor, a pressure sensor and a magnetic sensor, so as to achieve the corresponding intelligent feedback and control.

In some embodiments, the fiber core and the protective layer 4 or the intermediate layer 2 are in a slidable fit. The fiber core is slidable in the core layer 1 of controllably self-deformable optical fiber, thereby achieving focusing of a laser or allowing further penetration of the optical fiber into a narrow lacuna.

The controllably self-deformable element 3 provided herein has a small size and a relatively simple structure. The controllably self-deformable element 3 is made of metals, high-molecular polymers and biological materials, which are capable of deforming, such as stretching, bending, tightening, expanding and/or rotating under the exposure to sound, light, electricity, heat, magnetism and/or chemical substances. The materials include, but are not limited to mechanically deformable materials, pneumatically deformable materials, electro-deformable materials, hydraulically deformable materials, pneumatic-hydraulic hybrid deformable materials, artificial muscles and other polymer, metal and bio-flexible deformable materials with electric insulation, magnetic insulation, sound insulation, light insulation and thermal insulation. The electro-deformable materials include, but are not limited to, electrostrictive ceramics and polyurethane materials.

Figure 2:
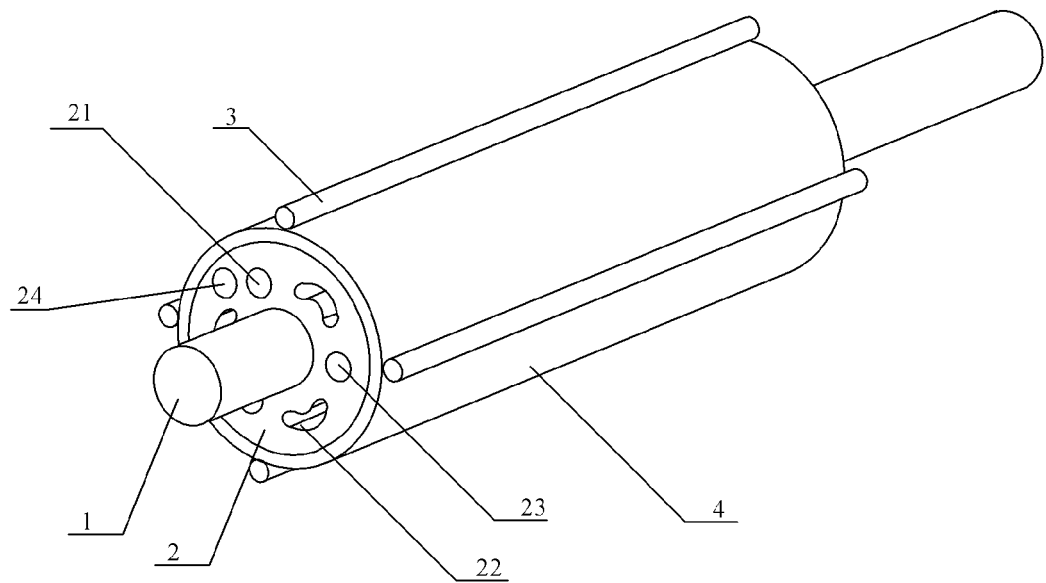
FIG. 2 is a schematic diagram of the controllably self-deformable optical fiber according to another embodiment of the present disclosure.

The controllably self-deformable element 3 can be of any shape, preferably an elongated shape shown in FIG. 1 or a long rod-like shape shown in FIG. 2. A long side of the controllably self-deformable element 3 is arranged along an axis of the protective layer 4. The controllably self-deformable optical fiber is provided with one or more controllably self-deformable elements 3, preferably a plurality of controllably self-deformable elements 3.

Figure 3:
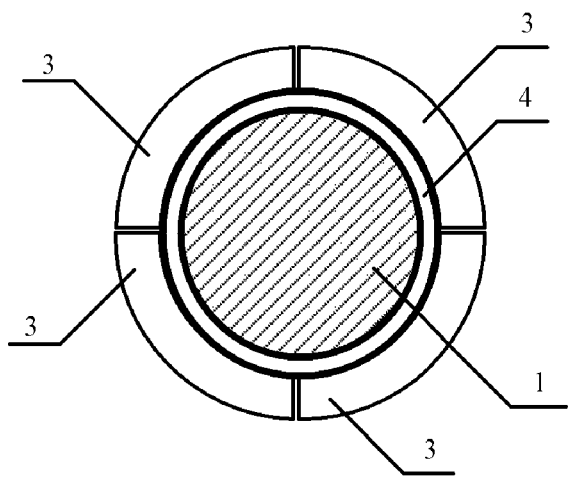
FIG. 3 is a cross-sectional view of the controllably self-deformable optical fiber according to an embodiment of the present disclosure, in which controllably self-deformable elements are uniformly distributed.

Referring to FIG. 3, the plurality of controllably self-deformable elements 3 can be uniformly distributed around the axis of the controllably self-deformable optical fiber or along the axis of the controllably self-deformable fiber. In addition, the plurality of controllably self-deformable elements 3 can be individually or jointly controlled to generate deformation. In this case, by controlling deformation and degree of deformation of the controllably self-deformable elements 3 distributed in certain positions, force generated by the deformation can force the controllably self-deformable optical fiber which is fixedly connected to them to passively produce the corresponding deformation, such as stretching or bending.

Figure 4:
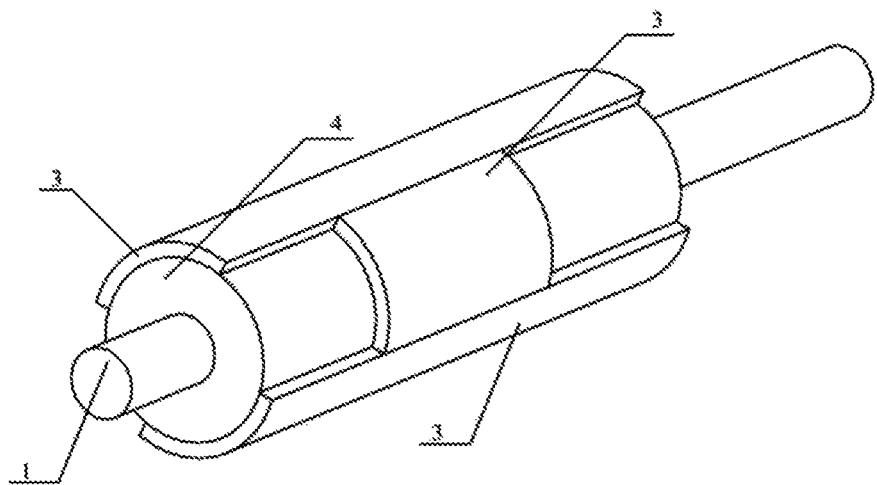
FIG. 4 is a schematic diagram of the controllably self-deformable optical fiber according to an embodiment of the present disclosure, in which the controllably self-deformable elements are unevenly distributed.
Figure 5:
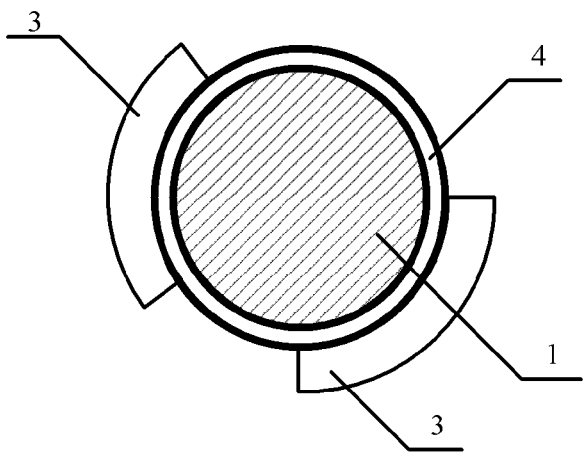
FIG. 5 is a cross-sectional view of the controllably self-deformable optical fiber according to an embodiment of the present disclosure, in which the controllably self-deformable elements are unevenly distributed.

Referring to FIGS. 4-5, the plurality of controllably self-deformable elements 3 can be unevenly distributed around the axis of the controllably self-deformable optical fiber or along the axis of the controllably self-deformable fiber. In addition, the plurality of controllably self-deformable elements 3 can be individually or jointly controlled to generate deformation. In this case, all controllably self-deformable elements 3 are jointly controlled to generate deformation, and the controllably self-deformable optical fiber is forced to have a preset deformation according to the distribution of the controllably self-deformable elements 3.

In some embodiments, shapes, sizes, quantities and attached positions of the controllably self-deformable elements 3 can be set in terms of different application requirements.

The controllably self-deformable element 3 is made of metals, high-molecular polymers and biological materials which are deformable, such as stretching, bending, tightening, expanding and/or rotating, under the exposure to sound, light, electricity, heat, magnetism and/or chemical substances. Because the physical or chemical factors applied to these materials are quantifiable and controllable, the deformation process and the deformation degree of the controllably self-deformable optical fiber are also controllable.

This application also provides a laser scalpel which includes the above-mentioned controllably self-deformable optical fiber.

This application further provides a laser processing device which includes the above-mentioned controllably self-deformable optical fiber.

The laser processing device can not only be applied in, such as oral root canal, pharynx, blood vessels, gastrointestinal tract, to precisely cut the lesion tissue in the narrow lacuna, but also can be used in industry. In the medical applications, based on the above-mentioned controllably self-deformable optical fibers, the laser processing device can stably reach narrow lacuna to precisely cut the diseased tissue with any shape. The laser processing device is provided with ultrashort pulse lasers, such as high-power and high-repetition-frequency femtosecond lasers. Laser beams are transmitted through the optical fibers, and the illuminating system and the imaging system are used for real-time monitoring. In addition, the laser processing device can be controlled to freely deform according to the morphology of the narrow lacuna, so as to reach the deepest working region.

The laser processing device may further include at least one control system. The control system is configured to control the tail end of the controllably self-deformable optical fiber, through sound, light, electricity, magnetism and/or chemical substances, to bend to gradually deepen along the curved morphology of the narrow lacuna, so that the entire tubular device is automatically controlled to reach the working face. When the fiber core is in slidable fit with the protective layer or the intermediate layer, the control system can also automatically control the fiber core to stretch by means of a motor and a steel wire, so as to reach a narrower lacuna.

In conclusion, the laser processing device including the controllably self-deformable optical fiber is applicable for surgical procedures in narrow and deep cavities, such as oral cavities, pharynx, blood vessels, tracheas and gastrointestinal tracts, and for precision preparation in industry. Compared with the light guide arm, the controllably self-deformable optical fiber is not only small in size, highly flexible and controllable, but also has multiple functions such as cutting, ablation, endoscopy, and free deformation, so that the controllably self-deformable optical fiber can cut any lesion in narrow and deep lacunae in any direction. In addition, the laser processing device can realize the precision cutting of the diseased tissue by controlling the femtosecond laser. At the same time, the laser processing device is provided with a monitoring device to realize safe control.

Described above are only preferred embodiments of this application, and are not intended to limit this application. Any modification, equivalent replacement and improvement made by those skilled in the art without departing from the spirit of this application shall fall within the scope of this application.

What is claimed is:

1. A controllably self-deformable optical fiber, comprising:
a core layer;

a protective layer; and a plurality of controllably self-deformable elements;

wherein the core layer comprises a fiber core and is provided inside the protective layer; and the plurality of controllably self-deformable elements are attached to an outer surface of the protective layer; and the plurality of controllably self-deformable elements are unevenly distributed around a central axis of the controllably self-deformable optical fiber; and the plurality of controllably self-deformable elements are individually controlled to generate deformation.

2. The controllably self-deformable optical fiber of claim 1, wherein the fiber core is a high-power laser fiber core, wherein the fiber core is a hollow fiber.

3. The controllably self-deformable optical fiber of claim 1, wherein the fiber core is in slidable fit with the protective layer or the intermediate layer.

4. The controllably self-deformable optical fiber of claim 1, wherein the controllably self-deformable element is made of a metal, a polymer or a biological material that is capable of stretching, bending, tightening, expanding and/or rotating, under the exposure to sound, light, electricity, heat, magnetism and/or chemical substances.

5. A laser scalpel, comprising the controllably self-deformable optical fiber of claim 1.

6. A laser processing device, comprising the controllably self-deformable optical fiber of claim 1.

7. The controllably self-deformable optical fiber of claim 1, further comprising: an intermediate layer;

wherein the intermediate layer is provided between the core layer and the protective layer; and a plurality of conduits which are parallel to a length direction of the core layer are provided in the intermediate layer.

8. The controllably self-deformable optical fiber of claim 7, wherein the plurality of conduits comprise a lighting fiber conduit; and a lighting fiber core is provided in the lighting fiber conduit.

9. The controllably self-deformable optical fiber of claim 7, wherein the plurality of conduits comprise an imaging fiber conduit; and an imaging fiber core is provided in the imaging fiber conduit.

10. The controllably self-deformable optical fiber of claim 7, wherein the plurality of conduits comprise at least one feed-discharge conduit for liquid and gas.

11. The controllably self-deformable optical fiber of claim 7, wherein the plurality of conduits comprise an electrical conduit; a sensor is provided at a tail end of the electrical conduit; and an electrical wire of the sensor is laid in the electrical conduit.

12. The controllably self-deformable optical fiber of claim 7, wherein the fiber core is in slidable fit with the protective layer or the intermediate layer.

* * * * *